United States Patent

Kamohara et al.

[11] Patent Number: 6,093,755
[45] Date of Patent: Jul. 25, 2000

[54] SILICONE COMPOSITION USEFUL FOR DENTAL TEMPORARY SEALING

[75] Inventors: Hiroshi Kamohara; Makiko Komoto; Ko Hinoura, all of Tokyo, Japan

[73] Assignee: GC Corporation, Tokyo, Japan

[21] Appl. No.: 08/982,433

[22] Filed: Dec. 2, 1997

[30] Foreign Application Priority Data

Dec. 11, 1996 [JP] Japan ................................. 8-346517

[51] Int. Cl.[7] ........................................................ C08K 3/02
[52] U.S. Cl. ...................... 523/118; 523/212; 523/120; 524/431; 524/493; 524/862; 528/15; 528/31
[58] Field of Search .................................. 523/118, 212, 523/120; 524/431, 493, 862; 528/15, 31

[56] References Cited

U.S. PATENT DOCUMENTS

| | | | |
|---|---|---|---|
| 4,035,453 | 7/1977 | Wittmair et al. | 524/862 |
| 4,550,030 | 10/1985 | Ohi et al. | 106/35 |
| 4,600,731 | 7/1986 | Louis et al. | 524/862 |
| 4,604,142 | 8/1986 | Kamohara et al. | 106/38.51 |
| 4,771,119 | 9/1988 | Wrobel | 524/862 |
| 4,814,011 | 3/1989 | Kamohara et al. | 106/38.51 |
| 4,909,847 | 3/1990 | Ohi et al. | 106/35 |
| 4,911,759 | 3/1990 | Ohi et al. | 106/35 |
| 5,203,914 | 4/1993 | Futami et al. | 523/109 |
| 5,328,974 | 7/1994 | McAfee | 524/431 |
| 5,631,320 | 5/1997 | Kamohara et al. | 524/789 |
| 5,637,628 | 6/1997 | Kamohara et al. | 523/109 |

*Primary Examiner*—Andrew E. C. Merriam
*Attorney, Agent, or Firm*—Oblon, Spivak, McClelland, Maier & Neustadt, P.C.

[57] ABSTRACT

A silicone composition useful for dental temporary sealing is disclosed, which comprises:

(A) 100 parts by weight of an organopolysiloxane having at least two aliphatic unsaturated hydrocarbons in one molecule and having a viscosity of from 50 to 1,000 cSt at 25° C.;

(B) from 0.1 to 40 parts by weight of an organohydrogenpolysiloxane having at least three hydrogen atoms directly bonded to a silicon atom in one molecule;

(C) from 10 to 500 ppm, based on the total amount of (A) and (B), of a silicone-soluble platinum compound;

(D) from 10 to 400 parts by weight of an inorganic filler; and (E) a finely powdered silica having a BET specific surface area of from 50 to 500 m$^2$/g, the surface of which is made hydrophobic.

4 Claims, No Drawings

SILICONE COMPOSITION USEFUL FOR DENTAL TEMPORARY SEALING

FIELD OF THE INVENTION

The present invention relates to a silicone composition useful for dental temporary sealing, which is used for the purpose of temporarily sealing the tooth cavity after cavity preparation in the dentistry.

BACKGROUND OF THE INVENTION

In the dental therapy, in case where the tooth caries area is restored by a metal cast, the tooth cavity after cavity preparation is often temporarily sealed with a temporary sealing material. For the purpose of this temporary sealing, there are included prevention of a foreign matter from entry into the cavity, protection against a stimulation from the outside, prevention of a dentin surface from contamination, and preservation of the occlusal relation, during a period of time up to the completion of a metal cast. As characteristics which a temporary sealing material to be used for such purpose should have, those set forth below can be enumerated. That is, it has good sealing properties; it can be readily removed; it has a strength to a some extent; and its temporary sealing operation is simple. Examples of temporary sealing materials which are used at present include thermoplastic stoppings comprising guttapercha as a chief material, zinc oxide eugenol cements, hydraulic temporary sealing material, and resin-based temporary sealing materials.

Though the stoppings are a material with high safety and can be extremely easily removed, they require not only a heating operation for softening but also skill in filling into the cavity so that if they fail in a filling timing, their sealing properties become extremely worse. Though the zinc oxide eugenol cements are a material with superior sealing properties, since their cured products are brittle, the removal operation thereof are difficult. Also, even if very small amounts of the zinc oxide eugenol cements attach to and remain in teeth, at the time of impression taking with a silicone impression material, they likely cause a delay of curing of the silicone impression material. Though the hydraulic temporary sealing materials are in a form of one paste, are cured by the moisture in the oral cavity, and are superior in the operability at the time of filling due to the nature of one paste, likewise the zinc oxide eugenol cements, their cured products are brittle so that the removal operation thereof are difficult. Further, though the resin-based temporary sealing materials are good in the operability, the characteristics are different among products, and their cured products are in general hard and brittle so that they are inferior in the operability of removal. In this case, while there are products having improved operability of removal by imparting softness to a some extent, it can not be said that such products having thorough capability. In addition, in recent years, as a new sealing process, there has been employed a process in which for the purpose of coating and protecting a dentin surface after the cavity preparation, the dentin surface in the cavity is previously subjected to one-layer coating with a resin having high fluidity, and a temporary sealing material is filled therein thereby effecting the temporary sealing has been employed. However, in this temporary sealing process, resin-based temporary sealing materials can not be used, and in case where a resin-based temporary material is used, the applied resin is adhered to the temporary sealing material, whereby the temporary sealing material can be no longer removed.

As described above, the temporary sealing materials which are used at present are not a product fully meeting the above-described characteristics, i.e., it has good sealing properties; it can be readily removed; it has a strength to a some extent; and its temporary sealing operation is simple. Especially, it is the present state that many of the products are difficult with respect to the removal operation, while those which can be readily removed are poor in the sealing properties.

SUMMARY OF THE INVENTION

Under such circumstances, the present invention is aimed to provide a temporary sealing material which does not require complicated operations such as the heating operation, has such a high hardness that it can resist the biting pressure, has good sealing properties, can be readily removed from the cavity, and even in case where the cavity is temporarily sealed upon coating with a resin, neither reacts with nor adheres to the resin.

The easiness of removal from the cavity depends upon the presence or absence of breakage at the time of removing the temporary sealing material as well as the close adhesion (or adhesion) to the cavity. That is, even in case where the temporary sealing material is likely broken, if it is poor in close adhesion to the cavity, it can be relatively readily removed. On the other hand, even in case where the temporary sealing material is hardly broken, if it firmly closely adheres to the cavity, it is difficult to remove the temporary sealing material. Thus, the present inventors took into account the mutual balance of them and made extensive and intensive investigations in order to develop a temporary sealing material having ideal characteristics as the temporary sealing material. As a result, they took note of the application of an addition type silicone having elasticity, the characteristic of which is quite different from the conventional temporary sealing materials, and having good release properties so that it is hardly broken and have been successful in developing a novel temporary sealing material capable of meeting all of the characteristics required for the temporary sealing material upon suitably controlling the both characteristics between the properties that it is hardly broken and the close adhesion, leading to the accomplishment of the present invention.

That is, according to the present invention, all of the characteristics required as a temporary sealing material can be satisfied, i.e., use of an organopolysiloxane having a specified viscosity as a substrate imparts a sufficient harness to a cured product; addition of an organohydrogenpolysiloxane as a crosslinking agent to be used for addition curing type silicones and a silicone-soluble platinum compound as a curing catalyst as well as an inorganic filler thereto imparts a viscosity and shaping properties suited for the operation of filling a kneaded paste; and use of a finely powdered silica, the surface of which is made hydrophobic, improves the tear strength of a cured product, thereby preventing the occurrence of breakage at the time of removing the temporary sealing material and improves the close adhesion of the temporary sealing material to the paste before curing and to the cavity after curing.

In addition, since the composition according to the present invention has a make-up quite different from that of resins which are usually used in the dentistry, even in case where a dentin surface in the cavity is temporarily sealed upon coating with a resin, the composition can be used with confidence without causing reaction with or adhesion to the coated resin. Also, the composition according to the present invention is not only good in close adhesion to the cavity and superior in marginal sealing properties but also free from dropping away at the time of biting so that it can keep a good biting state.

That is, a silicone composition useful for dental temporary sealing comprises:

(A) 100 parts by weight of an organopolysiloxane having at least two aliphatic unsaturated hydrocarbons in one molecule and having a viscosity of from 50 to 1,000 cSt at 25° C.;

(B) from 0.1 to 40 parts by weight of an organohydrogenpolysiloxane having at least three hydrogen atoms directly bonded to a silicon atom in one molecule;

(C) from 10 to 500 ppm, based on the total amount of (A) and (B), of a silicone-soluble platinum compound;

(D) from 10 to 400 parts by weight of an inorganic filler; and (E) a finely powdered silica having a BET specific surface area of from 50 to 500 $m^2/g$, the surface of which is made hydrophobic.

DETAILED DESCRIPTION OF THE INVENTION

In the silicone composition useful for dental temporary sealing according to the present invention, the component (A) is an organopolysiloxane having at least two aliphatic unsaturated hydrocarbons in one molecule and having a viscosity of from 50 to 1,000 cSt at 25° C. This organopolysiloxane is preferably one which is linear and in which the both terminal ends of the molecular chain thereof are hindered by a vinyl group, and the vinyl group may be contained in the chain. If the viscosity of the organopolysiloxane is less than 50 cSt, a cured product is brittle so that the operation for removing it is difficult. On the other hand, if the viscosity exceeds 1,000 cSt, the hardness of a cured product is low so that it is likely deformed due to the biting pressure. Therefore, the both cases are not desired.

The organohydrogenpolysiloxane as the component (B) has at least three hydrogen atoms directly bonded to a silicon atom in one molecule and functions as a crosslinking agent. If the amount of the organohydrogenpolysiloxane used is less than 0.1 par by weight based on 100 parts by weight of the component (A), not only the hardness of a cured product is low, but also the curing rate is low. On the other hand, if the amount of the component (B) exceeds 40 parts by weight, a cured product is very brittle. Therefore, the both cases are not desired.

Examples of the silicone-soluble platinum compound as the component (C) include known addition reaction catalysts such as chloroplatinic acid, alcohol-modified chloroplatinic acid, and complexes between chloroplatinic acid and olefins, with a vinylsiloxane complex of chloroplatinic acid being especially preferred. A suitable amount of the component (C) added is in the range of from 10 to 500 ppm based on the total amount of the foregoing components (A) and (B). If the amount of the component (C) is less than 10 ppm, not only the curing rate of the composition is low, but also in case where a substance which likely hinders the catalytic ability of this platinum compound is present in a trace amount, the curing of the composition is greatly delayed. On the other hand, if the amount of the component (C) exceeds 500 ppm, not only the curing rate of the composition is too high, but also the production cost is high, resulting in a disadvantage in economy. Therefore, the both cases are not desired. The silicone-soluble platinum compound including chloroplatinic acid is preferably used upon being dissolved in alcohol-based, ketone-based, ether-based, or hydrocarbon-based solvents, or polysiloxane oils.

Examples of the inorganic filler used as the component (D) include quartz, cristobalite, diatomaceous earth, fused quartz, titanium dioxide, and fused silica. A suitable amount of the inorganic filler is from 10 to 400 parts by weight based on 100 parts by weight of the component (A). If the amount of the component (D) is less than 10 parts by weight, a cured product is so soft that it can not resist the biting pressure. On the other hand, if the amount of the component (D) exceeds 400 parts by weight, not only the viscosity of the composition is too high so that the operation for filling the composition in the cavity is difficult, but also the close adhesion of the composition is remarkably low. Therefore, the both cases are not desired.

The finely powdered silica used as the component has a BET specific surface area of from 50 to 500 $m^2/g$, and its surface is made hydrophobic. This hydrophobic finely powdered silica is substantially obtained by thermally processing, for example, a fused silica as a hydrophilic silica with a surface processing agent such as methyltrichlorosilane, dimethyldichlorosilane, or trimethylchlorosilane, or corresponding alkoxysilanes, octamethylcyclotetrasiloxane, hexamethyldisiloxane, hexamethyldisilazane, or mixtures thereof, or with such a surface processing agent and water. Any hydrophobic silica in which all or almost all part of the active silanol groups on the surface thereof are hindered by a hydrophobic group such as a $(CH_3)_3SiO_{1/2}$ unit, a $(CH_3)_2SiO_{2/2}$ unit, and a $CH_3SiO_{3/2}$ unit can be used. This hydrophobic finely powdered silica is not only useful for improving the close adhesion of a cured product to the cavity but also effective for improving the tear strength of the cured product and hence, the cured product can be readily removed away at the time of removing the temporary sealing material without causing breakage. This hydrophobic finely powdered silica has a BET specific surface area of from 50 to 500 $m^2/g$. If the BET specific surface area of the hydrophobic finely powdered silica is less than 50 $m^2/g$, the close adhesion of the cured product to the cavity is not sufficient, and the tear strength is low. On the other hand, if the BET specific surface area exceeds 500 $m^2/g$, the viscosity of the paste increases, whereby it is difficult to undergo kneading and to filling the composition in the cavity. Therefore, the both cases are not desired. In addition, a suitable amount of the hydrophobic finely powdered silica to be compounded is from 5 to 50 parts by weight based on 100 parts by weight of the component (A). If the compounding amount of the hydrophobic finely powdered silica is less than 5 parts by weight, the close adhesion to the cavity and the tear strength are not sufficient. On the other hand, if it exceeds 50 parts by weight, the viscosity of the composition is too high, whereby it is difficult to undergo kneading. Therefore, the both cases are not desired.

If desired, various inorganic or organic coloring agents, nonionic surface active agents, and the like can be added so far as the characteristics of the composition according to the present invention are not impaired. Examples of the coloring agents which can be used include those which are used in the usual silicone compositions, such as red oxide, titanium white, titanium yellow, and cobalt blue, and examples of the nonionic surface active agents which can be used include those such as polyoxyethylene alkyl ethers and sorbitan fatty acid esters.

The present invention will be described below in more detail with reference to the following Examples, but it should not be construed that the invention is limited thereto.

EXAMPLE 1

A base paste and a catalyst paste each having the following make-up were prepared.

(Base Paste)

Dimethylpolysiloxane having a viscosity of 50 cSt at 25° C., in which the both terminal ends of the molecular chain thereof are hindered by a methylvinylsiloxy group: 100 parts by weight Linear methylhydrogenpolysiloxane containing 45 mole% of a methylhydrogensiloxane unit: 20 parts by weight Quartz: 20 parts by weight (Catalyst Paste)

Dimethylpolysiloxane having a viscosity of 50 cSt at 25° C., in which the both terminal ends of the molecular chain thereof are hindered by a methylvinylsiloxy group: 100 parts by weight Silicone oil solution containing 0.5% by weight of a 1,3-divinyltetramethyldisiloxane-platinum complex: 4 parts by weight Hydrophobic finely powdered silica having a BET specific surface area of 200 $m^2/g$, the surface of which is hindered by a $(CH_3)_3SiO_{1/2}$ unit: 100 parts by weight Subsequently, equal amounts of the above-described base paste and the above-described catalyst paste were taken and kneaded for 30 seconds by means of a spatula, and the kneaded mixture was poured into a mold having a height of 12 mm and a diameter of 30 mm, followed by allowing it to stand in a constant-temperature water bath at 37° C. for one day. Thereafter, a cured product was taken out from the mold, and its hardness was measured by means of a spring type hardness tester as described in JIS T6301. Similarly, a tear test specimen A type as described in JIS T6301 was used and after being allowed to stand in a constant-temperature water bath at 37° C. for one day, was subjected to a tear test. Also, a test for evaluating the close adhesion was carried out in the following manner. That is, the kneaded mixture was filled in the cavity formed on a lingual surface of bovine tooth and after being cured, was allowed to stand in a constant-temperature water bath at 37° C. for one day. Thereafter, the resulting assembly was subjected to a thermal cycle test 1,000 times by alternately dipping in a fuchsine solution at 4° C. and a fuchsine solution at 60° C. and observed for the degree of penetration of the pigment into the cavity, thereby evaluating the close adhesion (it is evaluated that the higher the degree of penetration of the pigment, the worse the close adhesion is). The test results are summarized and given in Table 1.

As shown in Table 1, the temporary sealing material according to the present make-up was high in hardness, could be readily removed away because of its high tear strength, and was superior in close adhesion.

EXAMPLE 2

A base paste and a catalyst paste each having the following make-up were prepared.

(Base Paste)

Dimethylpolysiloxane having a viscosity of 1,000 cSt at 25° C., in which the both terminal ends of the molecular chain thereof are hindered by a methylvinylsiloxy group: 100 parts by weight Linear methylhydrogenpolysiloxane containing 40 mole % of a methylhydrogensiloxane unit: 3 parts by weight Quartz: 800 parts by weight (Catalyst Paste)

Dimethylpolysiloxane having a viscosity of 1,000 cSt at 25° C., in which the both terminal ends of the molecular chain thereof are hindered by a methylvinylsiloxy group: 100 parts by weight Silicone oil solution containing 0.5% by weight of a 1,3-divinyltetramethyldisiloxane-platinum complex: 3 parts by weight Hydrophobic finely powdered silica having a BET specific surface area of 200 $m^2/g$, the surface of which is hindered by a $(CH_3)_3SiO_{1/2}$ unit: 10 parts by weight Subsequently, equal amounts of the above-described base paste and the above-described catalyst paste were taken and kneaded for 30 seconds by means of a spatula, and the kneaded mixture was subjected to various tests in the same manner as in Example 1. The test results are summarized and given in Table 1. As shown in Table 1, the temporary sealing material according to the present make-up was high in hardness, could be readily removed away because of its high tear strength, and was superior in close adhesion.

EXAMPLE 3

A base paste and a catalyst paste each having the following make-up were prepared.

(Base Paste)

Dimethylpolysiloxane having a viscosity of 500 cSt at 25° C., in which the both terminal ends of the molecular chain thereof are hindered by a methylvinylsiloxy group: 100 parts by weight Linear methylhydrogenpolysiloxane containing 50 mole % of a methylhydrogensiloxane unit: 10 parts by weight Quartz: 400 parts by weight (Catalyst Paste)

Dimethylpolysiloxane having a viscosity of 500 cSt at 25° C., in which the both terminal ends of the molecular chain thereof are hindered by a methylvinylsiloxy group: 100 parts by weight Silicone oil solution containing 0.5% by weight of a 1,3-divinyltetramethyldisiloxane-platinum complex: 3 parts by weight Hydrophobic finely powdered silica having a BET specific surface area of 200 $m^2/g$, the surface of which is hindered by a $(CH_3)_3SiO_{1/2}$ unit: 50 parts by weight Subsequently, equal amounts of the above-described base paste and the above-described catalyst paste were taken and kneaded for 30 seconds by means of a spatula, and the kneaded mixture was subjected to various tests in the same manner as in Example 1. The test results are summarized and given in Table 1. As shown in Table 1, the temporary sealing material according to the present make-up was high in hardness, could be readily removed away because of its high tear strength, and was superior in close adhesion.

Comparative Example 1

A base paste and a catalyst paste each having the following make-up were prepared.

(Base Paste)

Dimethylpolysiloxane having a viscosity of 500 cSt at 25° C., in which the both terminal ends of the molecular chain thereof are hindered by a methylvinylsiloxy group: 100 parts by weight Linear methylhydrogenpolysiloxane containing 50 mole % of a methylhydrogensiloxane unit: 3 parts by weight Quartz: 200 parts by weight (Catalyst Paste)

Dimethylpolysiloxane having a viscosity of 500 cSt at 25° C., in which the both terminal ends of the molecular chain thereof are hindered by a methylvinylsiloxy group: 100 parts by weight Silicone oil solution containing 0.5% by weight of a 1,3-divinyltetramethyldisiloxane-platinum complex: 3 parts by weight Subsequently, equal amounts of the above-described base paste and the above-described catalyst paste were taken and kneaded for 30 seconds by means of a spatula, and the kneaded mixture was subjected to various tests in the same manner as in Example 1. The test results are summarized and given in Table 1. As shown in Table 1, while the temporary sealing material according to the present make-up was high in hardness, since its tear strength was low, the temporary sealing material was likely broken so that its removal properties were remarkably inferior. Also, in the close adhesion test, the penetration of the pigment was observed over the whole of the cavity so that it was confirmed that the temporary sealing material according to the present make-up was inferior in close adhesion.

Comparative Example 2

A base paste and a catalyst paste each having the following make-up were prepared.
(Base Paste)
Dimethylpolysiloxane having a viscosity of 20,000 cSt at 25° C., in which the both terminal ends of the molecular chain thereof are hindered by a methylvinylsiloxy group: 100 parts by weight
Linear methylhydrogenpolysiloxane containing 50 mole % of a methylhydrogensiloxane unit: 3 parts by weight
Quartz: 200 parts by weight
(Catalyst Paste)
Dimethylpolysiloxane having a viscosity of 20,000 cSt at 25° C., in which the both terminal ends of the molecular chain thereof are hindered by a methylvinylsiloxy group: 100 parts by weight
Silicone oil solution containing 0.5% by weight of a 1,3-divinyltetramethyldisiloxane-platinum complex: 3 parts by weight
Hydrophobic finely powdered silica having a BET specific surface area of 200 m$^2$/g, the surface of which is hindered by a $(CH_3)_3SiO_{1/2}$ unit: 5 parts by weight Subsequently, equal amounts of the above-described base paste and the above-described catalyst paste were taken and kneaded for 30 seconds by means of a spatula, and the kneaded mixture was subjected to various tests in the same manner as in Example 1. The test results are summarized and given in Table 1. As shown in Table 1, while the temporary sealing material according to the present make-up was high in tear strength and good in close adhesion, since its cured product was low in hardness, it could not resist the biting pressure so that it might be possibly deformed or dropped. As a result of the close adhesion test, though the penetration of the pigment was found in a part of the cavity, the close adhesion was substantially good.

Comparative Example 3

A thermoplastic temporary sealing material comprising commercially available guttapercha as a chief material (a trade name "Temporary Stopping" made by GC Dental Industries) was heated for softening, and test samples were prepared therefrom and subjected to various tests in the same manner as in Example 1. The test results are summarized and given in Table 1. As shown in Table 1, while this temporary sealing material was high in hardness and could thoroughly resist the biting pressure, because of its low tear strength, its cured product was likely broken at the time of removal so that the operability of removal was extremely poor. Also, in the close adhesion test, the penetration of the pigment was observed over the whole of the cavity so that it was confirmed that this temporary sealing material was inferior in close adhesion.

TABLE 1

| | Hardness | Tear Strength (N/m$^2$) | Close Adhesion (penetration of pigment) |
|---|---|---|---|
| Example 1 | 80 | 8.0 | Good (No penetration of the pigment was observed.) |
| Example 2 | 76 | 9.2 | Good (No penetration of the pigment was observed.) |
| Example 3 | 78 | 8.5 | Good (No penetration of the pigment was observed.) |
| Comparative Example 1 | 75 | 4.5 | Poor (The penetration of the pigment was observed over the whole of the cavity.) |
| Comparative Example 2 | 52 | 6.0 | Substantially qood (The penetration of the pigment was partly observed.) |
| Comparative Example 3 | 80 | 1.5 | Poor (The penetration of the pigment was observed over the whole of the cavity.) |

As described above, the silicone composition useful for dental temporary sealing according to the present invention has superior abilities such that it is able to undergo temporary sealing through a simple operation, it is superior in close adhesion to the cavity, it is able to surely undergo marginal sealing thereby preventing a dentin from contamination, it has a harness sufficient for resisting the biting pressure, it is able to thoroughly preserve the occlusal state after sealing, and that because of its high tear strength, it can be readily removed away at the time of removal without causing breakage.

In addition, in case where a dentin surface in the cavity is temporary sealed upon coating with a resin, the present invention can be used with confidence without coating reaction with or adhesion to the coated resin.

In the light of the above, the silicone composition useful for dental temporary sealing according to the present invention is a novel and extremely useful temporary sealing material in the dentistry having superior characteristics overcoming the drawbacks of the conventional temporary sealing materials.

While the invention has been described in detail and with reference to specific embodiments thereof, it will be apparent to one skilled in the art that various changes and modifications can be made therein without departing from the spirit and scope thereof.

What is claimed is:

1. A silicone composition useful for dental temporary sealing, which comprises:
   (A) 100 parts by weight of an organopolysiloxane having at least two aliphatic unsaturated hydrocarbons in one molecule and having a viscosity of from 50 to 1,000 cSt at 25° C.;
   (B) from 0.1 to 40 parts by weight of an organohydrogenpolysiloxane having at least three hydrogen atoms directly bonded to a silicon atom in one molecule;
   (C) from 10 to 500 ppm, based on the total amount of (A) and (B), of a silicone-soluble platinum compound;
   (D) from 10 to 400 parts by weight of an inorganic filler selected from the group consisting of quartz, cristobalite, diatomaceous earch, fused quartz, titanium dioxide and fused silica; and (E) from 5 to 50 parts by weight, based on the amount of (A) of powdered silica having a BET specific surface area of from 50 to 500 m$^2$/g, the surface of which is hindered by a hydrophobic group selected from the group consisting of $(CH_3)_3SiO_{1/2}$ unit, $(CH_3)_2SiO_{2/2}$ unit and $(CH_3)SiO_{3/2}$ unit.

2. A silicone composition useful for dental temporary sealing as claimed in claim 1, wherein the organopolysiloxane (A) is a linear form and in which the both terminal ends of the molecular chain thereof are hindered by a vinyl group.

3. A silicone composition useful for dental temporary sealing as claimed in claim 1, wherein the organohydrogenpolysiloxane (B) is a linear methylhydrogenpolysiloxane.

4. A silicone composition useful for dental temporary sealing as claimed in claim 1, wherein the silicone-soluble platinum compound (C) is a vinylsiloxane complex of chloroplatinic acid.

* * * * *